(12) United States Patent
O'Lenick

(10) Patent No.: US 9,346,914 B1
(45) Date of Patent: *May 24, 2016

(54) PROPANE DIOL POLYESTERS

(71) Applicant: SurfaTech Corporation, Lawrenceville, GA (US)

(72) Inventor: Thomas George O'Lenick, Dacula, GA (US)

(73) Assignee: SURFATECH CORPORATION, Lawrenceville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/121,740

(22) Filed: Oct. 14, 2014

Related U.S. Application Data

(62) Division of application No. 13/986,020, filed on Mar. 25, 2013, now Pat. No. 8,912,233.

(60) Provisional application No. 61/689,981, filed on Jun. 18, 2012.

(51) Int. Cl.
*C08G 63/20* (2006.01)

(52) U.S. Cl.
CPC ..................................... *C08G 63/20* (2013.01)

(58) Field of Classification Search
CPC .. A01B 12/006; C08G 63/20; B05B 13/0431; B05B 13/0452; B05B 13/0468; B05B 15/12; B25J 18/005; G01N 33/56988; G01N 33/53; G01N 33/54306; Y10S 435/974; Y10S 435/961; Y10S 436/825; Y10S 436/826; A61K 8/37; A61K 8/85; A61Q 19/00; A61Q 5/12; C07C 69/34; C07C 69/74
See application file for complete search history.

(56) References Cited

U.S. PATENT DOCUMENTS 8,148,569 B1   4/2012   O'Lenick
8,912,233 B1 * 12/2014   O'Lenick ................. A61Q 5/12
                                                        514/574

\* cited by examiner

*Primary Examiner* — Yevegeny Valenrod
*Assistant Examiner* — Blaine G Doletski

(57) ABSTRACT

The present invention is directed toward a series of polyesters synthesized utilizing propane diol with tunable ascetics and performance in cosmetic formulation. These novel propane diol polyesters are designed to have great esthetics in cosmetic formulation. The physical properties and aesthetics of the current invention can be tuned rapidly by controlling the fatty groups, as well as the molecular weight of the polymer. The resulting propane diol polyesters have outstanding aesthetics and physical properties.

19 Claims, No Drawings

PROPANE DIOL POLYESTERS

RELATED APPLICATIONS

This application is a divisional patent application of Ser. No. 13/986,020 filed Mar. 25, 2013, which in turn claims priority to and benefit of U.S. Provisional Application No. 61/689,981 filed Jun. 18, 2012, the disclosure of which is incorporated herein for all purposes.

FIELD OF THE INVENTION

The present invention is directed toward a series of propane diol polyesters with tunable ascetics and performance in cosmetic formulation. These novel propane diol polyesters are designed to have tunable aesthetics. The physical and chemical properties of the current invention can be tuned rapidly by controlling the fatty group used, as well as the molecular weight of the polymer. Tuned here is meant the ability to adjust the physical properties to a desired value. The resulting propane diol polyesters have outstanding aesthetics and physical properties.

BACKGROUND OF THE INVENTION

Propane diol is a common material of natural origin. The structure is:

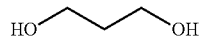

CAS Registry Number: 504-63-2 Index Name: Propane-1,3-diol.

Propane diol is made from corn syrup effected by a genetically modified strain of *E. Coli* developed by DuPont Tate & Lyle Bioproducts. Propane diol is mainly used in the production of polymers such as polytrimethylene terephthalate, and formulated into a variety of industrial products including adhesives, laminates, coatings, aliphatic polyesters and moldings. Polymers synthesized with propane diol are made in a variety of ways.

THE INVENTION

Object of the Invention

The current invention is directed toward a series of propane diol polyesters that are synthesized by the reaction of a diacid and propane diol end-capped with a mono-functional fatty alcohol. This end capping allows for the product to have great film forming ability and great aesthetics.

SUMMARY OF THE INVENTION

The present invention is related to a series of novel propane diol polyesters that are prepared by the reaction of propane diol, diacid and a mono-functional fatty alcohol. The mono-functional fatty alcohol has a duel purpose in this polymerization: mono-functional monomers are commonly used to control the molecular weight of the polymer chain and are often referred to as a chain terminator. Once the chain terminator reacts onto the polymer backbone, the polymerization ceases. Chain terminators, being mono-functional, always end up on the end of the polymer chain. For this reason, the selection of the fatty groups and the diacid will drastically change the physical properties and cosmetic aesthetics of the resulting material.

The compounds of the present invention are made by the polymerization of a diacid and propane diol and a fatty alcohol. The resulting polymer has the film forming ability of the propane diol polymer but the end capping by the mono-functional fatty alcohol. This combination of groups results in a high efficient deposition of the skin, hair and fibers.

These propane diol polyesters have the ability to tune the overall aesthetics of a formulation based on the alcohol and diacid used. This ability to tune the aesthetics is easily demonstrated when considering an example. Two propane diol polyesters with different alcohols (Region 1) were used. Dimer acid was utilized as the diacid. When considering the structure of the finished polymer, it is easy to see two distinct regions: Region 1 and Region 2. Below is the structure of the finished polymer.

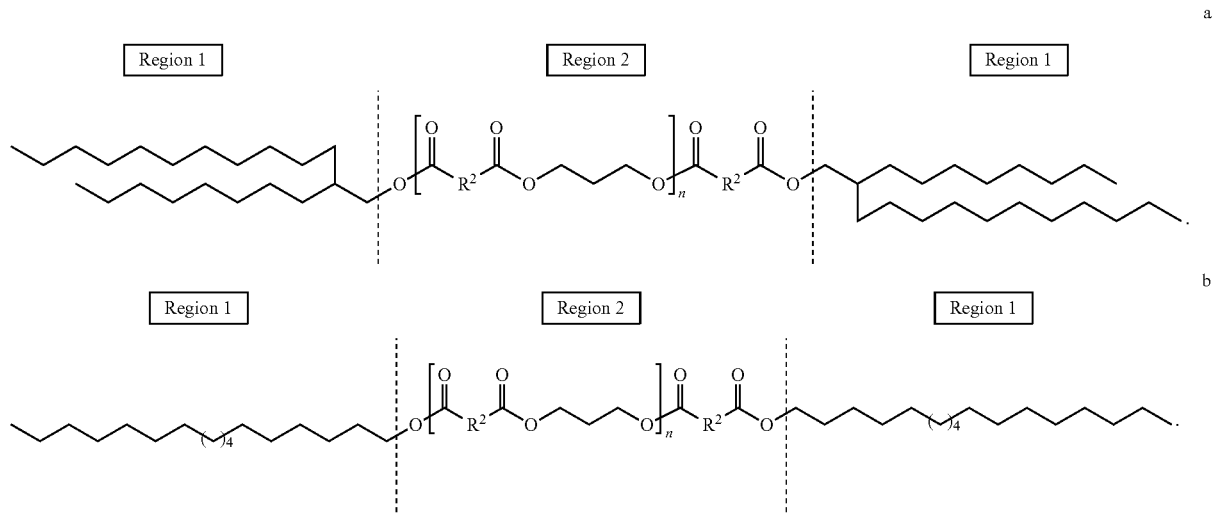

Polymer A was synthesized with a Guerbet alcohol containing 20 carbons, dimer acid and 1,3-propanediol. Region 1 in this example is a liquid that contains a dry feel on the skin. Region 2 is an amorphous polymer backbone that feels tacky on the skin and has limited solubility in polar esters. The finished polymer A is a transparent high viscosity liquid. In cosmetic formulation, this polymer gives a dry feel and provides a transfer restraint gloss. Polymer b was synthesized utilizing a linear fatty alcohol with 18 carbons, dimer acid and 1,3-propanediol. Region 1 in this polymer is a solid and feels waxy on the skin. Region 2 is an amorphous polymer backbone. The finished polymer is an opaque solid. It has very limited to no solubility in polar esters and in formulation gives a wax feel on the skin. While these two polymer (a & b) are very similar, they have very different physical properties and aesthetics.

DETAILED DESCRIPTION OF THE INVENTION

The present invention is aimed at a series of novel polyester derived from propane diol that provide desired esthetics and structure in cosmetic formulations.

Propane Diol Polyester

A propane diol polyester having the following structure:

$$R^1O-\left[\overset{O}{\underset{}{C}}-R^2-\overset{O}{\underset{}{C}}-O-CH_2CH_2CH_2-O-\overset{O}{\underset{}{C}}-R^2-\overset{O}{\underset{}{C}}-O\right]_n-R^2-\overset{O}{\underset{}{C}}-OR^1$$

wherein, $R^1$ is an alkyl containing 8 to 26 carbons, or mixtures thereof;

$R^2$ is independently selected from an alkyl containing 2 to 12 carbons, alkyl having the following structure:

$$\begin{array}{c}-CH_2\\|\\CH\\\nearrow\quad\searrow(CH_2)_4CH_3\\HC\quad\quad HC\\\|\quad\quad|\\HC\quad\quad HC-(CH_2)_7CH_2-\\\searrow\quad\nearrow\\CH\\|\\(CH_2)_4CH_3\end{array}\quad\text{or}\quad\begin{array}{c}-CH_2\\|\\CH\\\nearrow\quad\searrow(CH_2)_4CH_3\\H_2C\quad\quad HC\\|\quad\quad|\\H_2C\quad\quad HC-(CH_2)_7CH_2-\\\searrow\quad\nearrow\\CH\\|\\(CH_2)_4CH_3\end{array}$$

or mixtures thereof;

n is an integer ranging from 3 to 10.

Another aspect of the present invention is a process for conditioning skin, which comprises contacting the skin with an effective conditioning amount of a propane diol polyester having the following structure:

$$R^1O-\left[\overset{O}{\underset{}{C}}-R^2-\overset{O}{\underset{}{C}}-O-CH_2CH_2CH_2-O-\overset{O}{\underset{}{C}}-R^2-\overset{O}{\underset{}{C}}-O\right]_n-R^2-\overset{O}{\underset{}{C}}-OR^1$$

wherein, $R^1$ is an alkyl containing 8 to 26 carbons, or mixtures thereof;

$R^2$ is independently selected from an alkyl containing 2 to 12 carbons, or an alkyl having the following structure:

$$\begin{array}{c}-CH_2\\|\\CH\\\nearrow\quad\searrow(CH_2)_4CH_3\\HC\quad\quad HC\\\|\quad\quad|\\HC\quad\quad HC-(CH_2)_7CH_2-\\\searrow\quad\nearrow\\CH\\|\\(CH_2)_4CH_3\end{array}\quad\quad\begin{array}{c}-CH_2\\|\\CH\\\nearrow\quad\searrow(CH_2)_4CH_3\\H_2C\quad\quad HC\\|\quad\quad|\\H_2C\quad\quad HC-(CH_2)_7CH_2-\\\searrow\quad\nearrow\\CH\\|\\(CH_2)_4CH_3\end{array}$$

and mixtures thereof.

said effective conditioning concentration ranges from 0.1% to 25% by weight.

Preferred Embodiment

In a preferred embodiment $R^1$ is a branched alkyl containing 20 carbons.

In a more preferred embodiment $R^2$ is dimer acid.

In a more preferred embodiment $R^2$ is an alkyl having 18 carbons.

In a more preferred embodiment $R^1$ is a branched alkyl having 28 carbons.

In a more preferred embodiment $R^1$ is a branched alkyl having 32 carbons.

In a more preferred embodiment n is 5.

In a more preferred embodiment n is 10.

Raw Materials

Fatty Alcohols

Fatty alcohols are useful in the practice of the present invention are items of commerce they are available as either single components or mixtures.

Fatty alcohols are useful as raw materials in the preparation of compounds of the present invention are commercially available from a variety of sources including Procter and Gamble of Cincinnati Ohio.

The structures are well known to those skilled in the art.

| | R—OH Saturated | | |
|---|---|---|---|
| Example | R Formula | Common Name | Molecular Weight |
| 1 | $C_8H_{18}$ | Capryl | 130 |
| 2 | $C_{10}H_{22}$ | Capric | 158 |
| 3 | $C_{12}H_{25}$ | Lauryl | 186 |
| 4 | $C_{14}H_{30}$ | Myristyl | 214 |
| 5 | $C_{15}H_{32}$ | Pentadecyl | 229 |
| 6 | $C_{16}H_{34}$ | Cetyl | 243 |
| 7 | $C_{18}H_{36}$ | Stearyl | 269 |
| 8 | $C_{20}H_{40}$ | Arachidyl | 297 |
| 9 | $C_{22}H_{44}$ | Behenyl | 325 |
| 10 | $C_{26}H_{52}$ | Cetryl | 381 |
| 11 | $C_{34}H_{68}$ | Geddyl | 493 |

| | Unsaturated | | |
|---|---|---|---|
| Example | R Formula | Common Name | Molecular Weight |
| 12 | $C_{18}H_{36}$ | Oleyl | 268 |
| 13 | $C_{18}H_{34}$ | Linoleyl | 266 |

Example 14

Propane Diol

Propane diol is useful as raw materials in the preparation of compounds of the present invention. Propane diol is commercially available from DuPont Tate Lyle of Bloomington, Del.

The structures are well known to those skilled in the art.

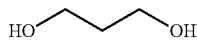

Example 15

Dimer Acid

Dimer acid is an item of commerce available commercially from Cognis Corporation. It conforms to the following structure:

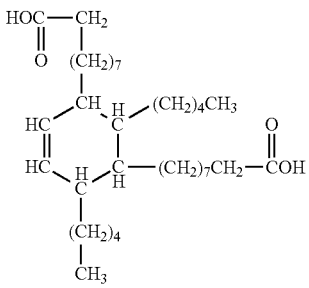

Example 16

Hydrogenated Dimer Acid

Hydrogenated dimer acid is an item of commerce available commercially from Henkel Corporation. It conforms to the following structure:

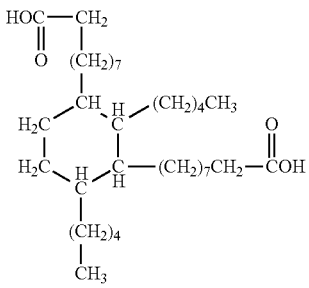

Dicarboxylic Acid

Dicarboxylic acid useful as raw materials in the synthesis of the compounds of the present invention are commercially available from a variety of sources including Cognis. They conform to the following structure;

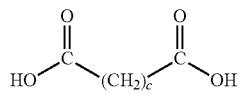

wherein;
c is an integer ranging from 1 to 10.

| Saturated Dicarboxylic acids | | | |
|---|---|---|---|
| Example | Common Name | c | Molecular Weight |
| 17 | Malonic | 1 | 104 |
| 18 | Succinic | 2 | 118 |
| 19 | Glutaric | 3 | 132 |
| 20 | Adipic | 4 | 146 |
| 21 | Pimelic | 5 | 160 |
| 22 | Subric | 6 | 174 |
| 23 | Azelaic | 7 | 188 |
| 24 | Sebacic | 8 | 202 |
| 25 | Undecanedioic | 9 | 216 |
| 26 | Dodecanedioic | 10 | 230 |

Guerbet Alcohols

Guerbet alcohols useful as raw materials in the preparation of compounds of the present invention are commercially available from a variety of sources including Sasol North America Incorporated of Houston Tex., and Jarchem located in Newark N.J.

The structures are well known to those skilled in the art.

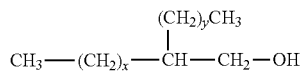

y is an integer ranging from 3-15 and x is an integer ranging from 5-17.

| Example | y | X |
|---|---|---|
| 27 | 9 | 7 |
| 28 | 11 | 13 |
| 29 | 13 | 15 |

General Procedure

A specified number of grams propane diol (example 14) is added to a specified amount of Guerbet alcohol (examples 27-29) and a diacid (examples 15-26). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | Di-acid | | Fatty Alcohol | | Propane Diol |
|---|---|---|---|---|---|
| Example | Example | Grams | Example | Grams | Grams |
| 30 | 15 | 183.1 | 29 | 47.6 | 19.3 |
| 31 | 15 | 198.9 | 29 | 28.2 | 22.9 |
| 32 | 15 | 194.4 | 9 | 35.1 | 20.5 |
| 33 | 15 | 206.0 | 9 | 20.3 | 23.7 |
| 34 | 15 | 187.5 | 28 | 42.7 | 19.8 |
| 35 | 15 | 201.7 | 28 | 25.1 | 23.2 |
| 36 | 15 | 196.7 | 27 | 32.6 | 20.8 |

-continued

| Example | Di-acid Example | Grams | Fatty Alcohol Example | Grams | Propane Diol Grams |
|---|---|---|---|---|---|
| 37 | 15 | 207.4 | 27 | 18.7 | 23.9 |
| 38 | 23 | 115.4 | 29 | 95.7 | 38.9 |
| 39 | 23 | 137.4 | 29 | 62.1 | 50.5 |
| 40 | 23 | 121.1 | 28 | 88.1 | 40.8 |
| 41 | 23 | 141.7 | 28 | 56.2 | 52.1 |
| 42 | 23 | 134.0 | 27 | 70.8 | 45.2 |
| 43 | 23 | 151.0 | 27 | 43.5 | 55.5 |
| 44 | 16 | 206.9 | 3 | 21.3 | 21.8 |
| 45 | 16 | 213.5 | 3 | 11.9 | 24.5 |
| 46 | 18 | 108.9 | 7 | 82.7 | 58.4 |
| 47 | 18 | 125.0 | 7 | 51.8 | 73.2 |
| 48 | 20 | 114.9 | 9 | 85.3 | 49.8 |
| 49 | 20 | 133.1 | 9 | 53.9 | 63.0 |
| 50 | 16 | 196.8 | 27 | 32.5 | 20.7 |
| 51 | 16 | 207.5 | 27 | 18.7 | 23.8 |
| 52 | 18 | 92.8 | 28 | 107.4 | 49.8 |
| 53 | 18 | 112.8 | 28 | 71.2 | 66.0 |
| 54 | 20 | 99.9 | 29 | 106.8 | 43.3 |
| 55 | 20 | 121.6 | 29 | 70.9 | 57.5 |

The compounds of the present invention are oily materials that provide conditioning to skin. They retard transepidermal water loss, and provide a water resistant barrier on the skin. In emulsions, they provide a water resistance holding actives on the skin. The actives include sunscreen actives, antioxidants, peptides and vitamins.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polyester composition made by the reaction of:
(A) a fatty alcohol having the following structure:

R—OH wherein:
R is alkyl having 8 to 34 carbon atoms;
(B) 1,3 propane diol having the following structure:

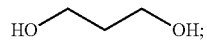

(C) a diacid selected from the group consisting of
(i) dimer acid having the following structure:

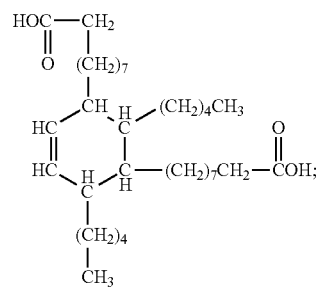

(ii) hydrogenated dimer acid having the following structure:

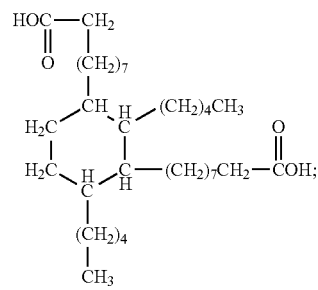

and
(iii) mixtures thereof.

2. The polyester composition of claim 1 wherein said diacid is (i).
3. The polyester composition of claim 2 wherein R is alkyl having 8 carbon atoms.
4. The polyester composition of claim 2 wherein R is alkyl having 12 carbon atoms.
5. The polyester composition of claim 2 wherein R is alkyl having 14 carbon atoms.
6. The polyester composition of claim 2 wherein R is alkyl having 16 carbon atoms.
7. The polyester composition of claim 2 wherein R is alkyl having 18 carbon atoms.
8. The polyester composition of claim 2 wherein R is alkyl having 20 carbon atoms.
9. The polyester composition of claim 2 wherein R is alkyl having 22 carbon atoms.
10. The polyester composition of claim 2 wherein R is alkyl having 34 carbon atoms.
11. A polyester composition of claim 1 wherein said diacid is (ii).
12. The polyester composition of claim 2 wherein R is alkyl having 8 carbon atoms.
13. The polyester composition of claim 2 wherein R is alkyl having 12 carbon atoms.
14. The polyester composition of claim 2 wherein R is alkyl having 14 carbon atoms.
15. The polyester composition of claim 2 wherein R is alkyl having 16 carbon atoms.
16. The polyester composition of claim 2 wherein R is alkyl having 18 carbon atoms.
17. The polyester composition of claim 2 wherein R is alkyl having 20 carbon atoms.
18. The polyester composition of claim 2 wherein R is alkyl having 22 carbon atoms.

19. The polyester composition of claim 2 wherein R is alkyl having 34 carbon atoms.

* * * * *